US010639478B2

(12) United States Patent  
Cuchiara et al.

(10) Patent No.: US 10,639,478 B2  
(45) Date of Patent: May 5, 2020

(54) ENHANCING LEFT VENTRICULAR RELAXATION THROUGH NEUROMODULATION

(71) Applicant: NeuroTronik IP Holding (Jersey) Limited, St. Helier (JE)

(72) Inventors: Michael Cuchiara, Durham, NC (US); Stephen C Masson, Raleigh, NC (US)

(73) Assignee: NeuroTronik IP Holding (Jersey) Limited, St. Helier (JE)

(*) Notice: Subject to any disclaimer, the term of this patent is extended or adjusted under 35 U.S.C. 154(b) by 130 days.

(21) Appl. No.: 15/884,812

(22) Filed: Jan. 31, 2018

(65) Prior Publication Data

US 2018/0214698 A1 Aug. 2, 2018

Related U.S. Application Data

(60) Provisional application No. 62/452,354, filed on Jan. 31, 2017.

(51) Int. Cl.  
*A61N 1/36* (2006.01)  
*A61M 1/12* (2006.01)  
*A61N 1/05* (2006.01)

(52) U.S. Cl.  
CPC ......... *A61N 1/36114* (2013.01); *A61M 1/122* (2014.02); *A61M 1/125* (2014.02); *A61N 1/0551* (2013.01); *A61N 1/36139* (2013.01); *A61M 2205/054* (2013.01); *A61N 1/36153* (2013.01); *A61N 1/36157* (2013.01); *A61N 1/36171* (2013.01); *A61N 1/36175* (2013.01); *A61N 1/36185* (2013.01)

(58) Field of Classification Search  
USPC .......................................................... 607/9  
See application file for complete search history.

(56) References Cited

U.S. PATENT DOCUMENTS

2004/0215049 A1* 10/2004 Zdeblick ............ A61B 5/02028  
                                                                             600/16  
2013/0072997 A1* 3/2013 Sanders ............. A61N 1/36053  
                                                                             607/18

\* cited by examiner

*Primary Examiner* — Brian T Gedeon  
*Assistant Examiner* — Philip C Edwards

(57) ABSTRACT

Neuromodulation is used to enhance left ventricular relaxation. An exemplary neuromodulation system includes a therapy element positionable in proximity to at least one nerve fiber, and a stimulator configured to energize the therapy element to delivery therapy to the at least one nerve fiber such that left ventricular relaxation and left ventricular contractility are contemporaneously enhanced.

20 Claims, 3 Drawing Sheets

ENHANCING LEFT VENTRICULAR RELAXATION THROUGH NEUROMODULATION

This application claims the benefit of U.S. Provisional Application No. 62/452,354, filed Jan. 31, 2017

TECHNICAL FIELD OF THE INVENTION

The present application generally relates to systems and methods for neuromodulation.

BACKGROUND

U.S. Pat. No. 9,067,071 (the '071 patent), U.S. application Ser. No. 14/642,699, filed Mar. 9, 2015 (the "699 application"), U.S. application Ser. No. 14/801,560, filed Jul. 16, 2015 (the "'560 application"), U.S. application Ser. No. 14/820,536, filed Aug. 6, 2015 (the "'536 application"), and U.S. application Ser. No. 15/098,237, filed Apr. 13, 2016 describe systems which may be used for hemodynamic control in the acute hospital care setting, by transvascularly directing therapeutic stimulus to parasympathetic nerves and/or sympathetic cardiac nerves using one or more therapeutic elements (e.g. electrodes or electrode arrays) positioned in the neighboring vasculature. Each of the above-referenced applications is incorporated herein by reference.

In accordance with a method described in the '071 patent, autonomic imbalance in a patient may be treated by energizing a first therapeutic element disposed in the vasculature to deliver therapy to a parasympathetic nerve fiber such as a vagus nerve and energizing a second therapeutic element disposed in the vasculature to deliver therapy to a cardiac sympathetic nerve fiber. Delivery of the parasympathetic and sympathetic therapy decreases the patient's heart rate (through the delivery of therapy to the parasympathetic nerves) while at the same time elevating or maintaining the blood pressure (through the delivery of therapy to the cardiac sympathetic nerves) of the patient in treatment of heart failure. For treatment of acute heart failure syndromes, the neuromodulation therapy may be used to lower heart rate and increase cardiac contractility.

The '071 patent describes a neuromodulation system having a parasympathetic therapy element adapted for positioning within a blood vessel, a sympathetic therapy element adapted for positioning with the blood vessel; and a stimulator configured to energize the parasympathetic therapy element to deliver parasympathetic therapy to a parasympathetic nerve fiber disposed external to the blood vessel and to energize the sympathetic therapy element within the blood vessel to deliver sympathetic therapy to a sympathetic nerve fiber disposed external to the blood vessel. In other methods of transvascular nerve capture, including some described in the '699 and '560 applications, therapy may be delivered using multiple therapeutic elements positioned in different blood vessels. For example, one therapeutic element may be positionable within a first blood vessel to capture a first nervous system target outside the first blood vessel, and the other may be positionable in a second, different, blood vessel to capture a second nervous system target outside the second blood vessel.

A neuromodulation system used for the therapy may include an external pulse generator/stimulator that is positioned outside the patient's body. The therapeutic elements may be carried by one or more percutaneous catheters that are coupled to the external pulse generator. In other embodiments an implantable stimulator may instead be used, in which case the therapeutic elements may be disposed on leads electrically coupled to the implantable stimulator/pulse generator. The stimulator/pulse generator is configured to energize the therapeutic elements to transvascularly capture the target nerve fibers.

Left ventricular contractility ("LV contractility" or "LVC") is the strength and vigor with which the left ventricle of the heart contracts during systole. The greater the contractility the greater the stroke volume of blood per contraction of the heart. Since cardiac output ("CO") is the product of stroke volume and heart rate, greater contractility of the left ventricle correlates to greater cardiac output ("CO").

Left ventricular relaxation ("LV relaxation" or "LVR") is the relaxation of the muscle of the left ventricle during diastole. Rapid relaxation of the left ventricle is important for proper functioning of the heart. It helps to draw blood into the ventricle and allows more complete filling of the left ventricle. Slow LVR can cause congestion and thus increased pressure in the pulmonary circuit, and insufficient filling of the left ventricle. Some medical conditions, such as heart failure with preserved ejection fraction, can result in a reduction of LVR. Some treatments may cause an increase in contractility without causing a corresponding increase in relaxation. For example, heart failure patients are often treated using administration of inotropes, a treatment that increases contractility with the goal of increasing cardiac output, but because they do not cause a corresponding increase in relaxation, the left ventricle may not be able to fill adequately and cardiac output can remain compromised.

DETAILED DESCRIPTION

Figure 1:
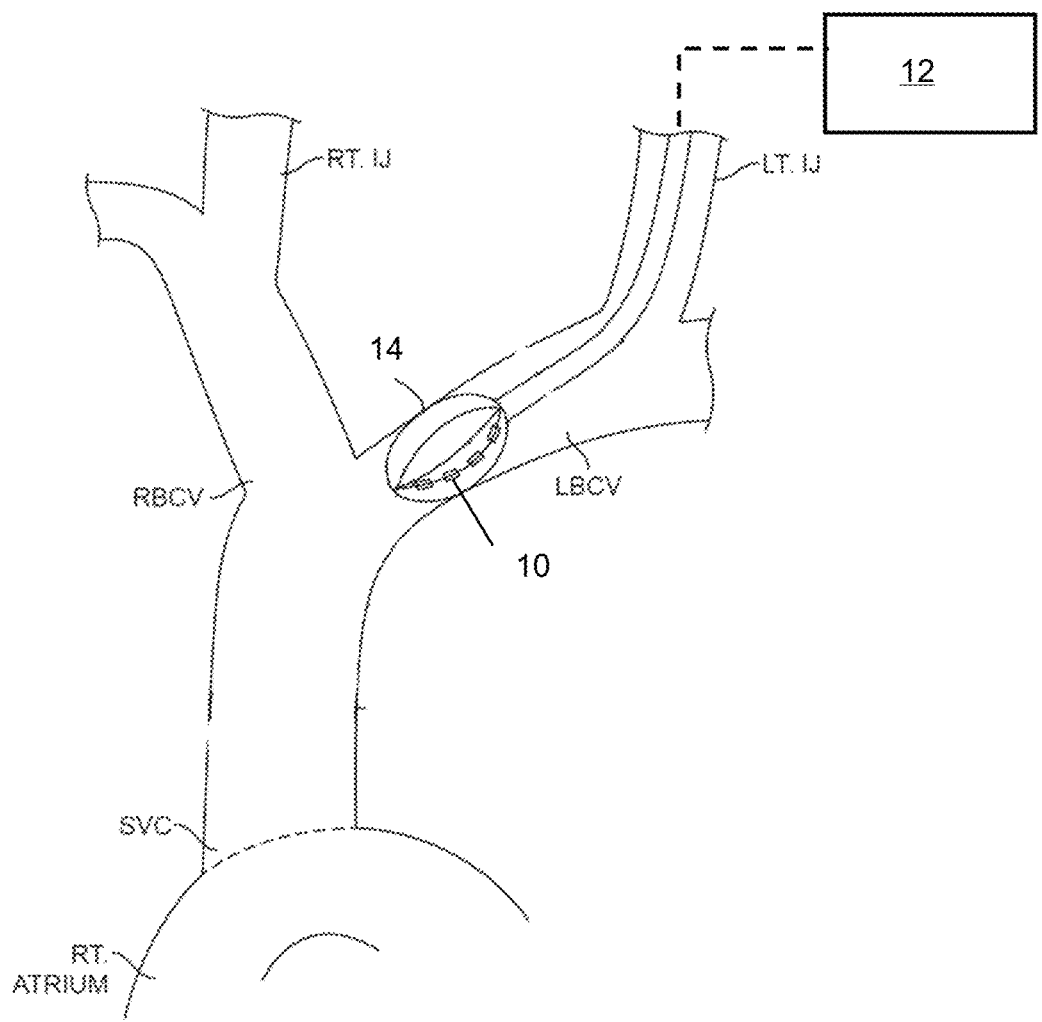
FIG. 1 shows a first embodiment of a neuromodulation system.

This application describes the use of neuromodulation to enhance, to a similar degree, contractility of the left ventricle in systole, and relaxation of the left ventricle in diastole. This application also describes the use of neuromodulation to enhance LVR, a therapy that may be combined with other therapies that enhance LVC, such as administration of inotropes.

Use of neuromodulation to enhance LVR causes the left ventricle to relax more quickly in diastole and has several benefits:
  more rapid relaxation of the LV increases the rate at which blood is drawn through the mitral valve into the left ventricle ("LV"), decreasing congestion in the pulmonary circuit more effectively or more quickly, and reducing pressure in the pulmonary circuit.
  more rapid relaxation of the LV causes more rapid filling of the LV, and consequently results in an increase in the volume of blood that fills the LV (compared with the volume that can be achieved without the enhanced relaxation achieved from the neuromodulation therapy);
  enhanced myocardial energetics—or an increase in the efficiency at which the tissue of the heart utilizes oxygen. In contrast, conventional heart failure treatments involving administration of inotropes to the patient will increase contractility but do not increase relaxation to a similar extent. Conventional heart failure treatments involving administration of inotropes that result in poor contractility relaxation balance have the disadvantage that they increase the amount of oxygen consumed by the myocardial tissue. Therefore, neuromodulation that can increase contractility (and thus CO) while augmenting relaxation to a similar degree also enhances myocardial energetics.

The impact of therapy on LVR is assessed by looking at a measure of LV relaxation, such as any of the following values:
  dP/dt min of LV pressure (LVP) drop in early diastole;
  tau (time constant of LV isovolumetric relaxation in diastole);
  arterial blood pressure (ABP) dP/dt min in early diastole; or
  ABP tau (time constant of ABP isovolumetric relaxation in diastole); or
  mitral valve deceleration time or mitral valve velocity time interval, determined using Doppler echocardiography.

The end diastolic pressure volume relationship (EDPVR)
The impact of therapy on LVC is assessed by looking at a measure of LV contractility, such as:
  dP/dt max of LV pressure rise in early systole;
  the value of LV stroke volume with a fixed pre-load (i.e. left ventricular end diastolic pressure)
  the value of stroke volume with a fixed afterload (i.e. systemic vascular resistance)
  the end systolic pressure volume relationship (ESPVR)

The embodiments below describe neuromodulation systems for enhancing LVR, or LVR and LVC, alone or in combination with other therapies such as mechanical hemodynamic support or pharmaceutical interventions.

First Embodiment: LV Relaxation Enhancement System

In a first embodiment, neuromodulation is used to deliver a therapy that enhances LVR. The neuromodulation may be carried out using one or more therapy elements positioned in intravascular sites, such as in venous blood vessels superior to the heart, with the therapy elements used to neuromodulate extravascular nerve fibers to achieve LVR enhancement. Suitable sites for the therapy elements include those described in U.S. patent application Ser. Nos. 14/642,699 and 14/801,560 or U.S. Pat. No. 9,067,071, such as the superior vena cava, left brachiocephalic vein, lower internal jugular vein, right brachiocephalic vein, azygos vein or azygos arch. Placement of therapy elements such as electrodes against the posterior portions of these blood vessels can be particularly advantageous for allowing capture of nerve fibers for LVR enhancement.

In general, an exemplary neuromodulation system 100 for enhancing LVR in accordance with the first embodiment may include, as shown in FIG. 1, one or more parasympathetic therapy elements 10 and a stimulator 12. The parasympathetic therapy element 10 is adapted to be positioned where it can (when energized) capture a parasympathetic nerve fiber, such as a cardiac branch of the vagus nerve or the main vagus nerve. The stimulator 12 is operable to energize the parasympathetic therapy element to deliver parasympathetic therapy to the parasympathetic nerve fiber so as to increase LV relaxation in diastole.

Preferred embodiments have therapy elements configured to be positioned within a blood vessel and energizeable to capture target nerve fibers outside the vessel, but alternative therapy elements include those configured to be positioned in locations other than blood vessels. Examples include electrodes that are positioned in direct contact with the nerve fibers or elsewhere in the extravascular space.

The therapy elements may be electrodes or electrode arrays, although it is contemplated that other forms of therapeutic elements (including, but not limited to, ultrasound, thermal, or optical elements) may instead be used. The therapy elements are preferably positioned on a flexible percutaneous catheter that includes an expandable support 14 for biasing the therapy elements (electrodes) into contact with the interior surface of the blood vessel. This optimizes conduction of neuromodulation energy from the electrodes to the target nerve fibers outside the vasculature. Expandable "basket" type catheter arrays may be used, as well as various other electrode and catheter designs known in the art. Some examples of catheters and electrode configurations that may be used are described in the applications referenced in the Background. Although FIG. 1 shows electrodes on only one strut, electrodes may be positioned on one or more of the struts in the basket configuration shown in FIG. 1.

The stimulator 100 may be an external device that is positioned outside the patient's body, although in modified embodiments an implantable stimulator may instead be used, in which case each the percutaneous catheter may be replaced with leads.

The system may use a control system that can control the therapy to achieve a desired effect with regard to LV relaxation. For example, the user might be prompted to input or select from a menu any of the following target parameters:
  the desired range for the measure of LVR (which measure may be, for example, the dP/dt min of LVP drop in early diastole, or the dP/dt min of arterial blood pressure drop in early diastole, or tau, the time constant for LV isovolumetric relaxation in diastole
  the desired percentage increase (or range of percentage increase) in the value of the selected measure of LVR relative to the value prior to initiation of the neuromodulation therapy (e.g. where the percentage increase is determined by comparing the pre-neuromodulation dP/dt min of LVP pressure drop in early diastole, with the dP/dt min of LVP pressure drop in early diastole during or after the neuromodulation)
  the desired percentage increase (or range of percentage increase) in the value of the rate of ABP relaxation relative to the rate prior to initiation of the neuromodulation therapy (like the above example but using the dP/dt min of ABP drop in early diastole as measured prior to and then during/after the neuromodulation)
  the desired percentage decrease (or range of percentage decrease) in the value of the time constant tau relative to the value of the time constant tau prior to initiation of the neuromodulation therapy
  the desired range for the ratio of the measure of LVC increase (as measured for example by the dP/dt max of left ventricle pressure rise in early systole) to the measure of LVR increase The first four inputs pertain to enhancement of LVR. The fifth pertains to enhancement of LVC. In some uses of the first embodiment, enhancement of LVC may come from the use of inotropes (discussed at the end of this section). The type measure for LVR and LVC may be selectable by the user or the system may be pre-configured to rely on certain measures of LVR and LVC.

The stimulator 100 may include a control system that includes a Parasympathetic Control function, a Parasympathetic Stimulation Output function, an Electrode Switching function.

The system may include or be used in conjunction with patient and system feedback elements that sense, measure, or derive various patient and system conditions and provide this information to the Parasympathetic Control function. These feedback elements may include sensors on the therapy catheter (or on separately placed catheters) such as pressure sensors, flow sensors, thermal sensors, PO2 sensors, mechanical interacting component, magnetic components, as well as the therapeutic electrodes and additional sensing electrodes. In addition, clinical sensors used directly on the patient such as arterial pressure transducers, heart rate, ECG electrodes, echocardiographic-based measurements and other hemodynamic monitors can be utilized and connected to the external stimulator. An Arterial Blood Pressure Sensor function in the neuromodulation system's control system can be connected to a standard arterial line pressure transducer and used to determine BP and HR. Therapy catheter electrodes or surface ECG electrodes can be connected to an ECG analyzer function of the control system that would derive ECG parameters such as HR, P and R-wave timing, refractory timing, and presence of cardiac arrhythmias, such as tachycardia or fibrillation, can be utilized as inputs to the system or for safety monitoring. Other hemodynamic sensors can be used to sense or derive hemodynamic parameters (such as flow rates, cardiac output, temperature, PO2 etc. described above) can be used both for closed-loop control, as well as safety monitoring. A central venous pressure sensor can provide feedback both on the therapy catheter's position, as well as hemodynamic feedback that can be utilized as part of the closed-loop control system.

The Parasympathetic Output functions generate the therapeutic stimuli which, in the exemplary embodiment, are electrical pulses. This output function can generate therapeutic levels (for example, electrical currents, voltages, and pulse widths), timing (frequencies, triggers, or gates to other timing such as ECG events, polarity (as applicable) and other parameters (e.g. effective electrode surface area and/or spacing as described in U.S. Ser. No. 15/098,237) to achieve the target parameters. The Electrode Switching function provides the means to connect the Parasympathetic Output function to the desired electrodes on the catheter support so as to capture the target parasympathetic cardiac nerves fibers. The selection of which connection or connections to make is determined during the response mapping procedure, which is like that described in U.S. Pat. No. 9,067,071.

The Parasympathetic Control functions implements the system's overall function based on user inputs and feedback from patient sensed or derived hemodynamic parameters. The Parasympathetic Control function directly governs the therapeutic output from the Parasympathetic Output function by controlling the therapeutic levels, timing, polarity, and other parameters. The Control function is responsible for the closed-loop modulation of LV relaxation as well as the response mapping function. In one example, the Parasympathetic Control function implements closed loop modulation utilizing the user-targeted parameters discussed above, as well as the feedback from actual LV relaxation (as measured for example by the rate dP/dt min of LV pressure drop in early diastole) and, as applicable, LVC (measured for example by the rate dP/dt max of left ventricle pressure rise in early systole). Also, in other examples, HR, BP and additional sensed and/or derived hemodynamic parameters (such as flow rates, cardiac output, LVP, ABP, tau, and Doppler echocardiographic-based measures etc. described above) can also be determined by the system and used to control the therapy.

The control system elements or functions can be implemented individually as or any combination of electronic circuitry, computer subsystems, computer software, mechanical subsystems, ultrasound subsystems, magnetic subsystems, electromagnetic subsystems, optical subsystems, and a variety of sensors or detectors including, but not limited to, electromechanical sensors, electrochemical sensors, thermal sensors, and infrared sensors. In each embodiment, the control system elements or functions communicate with each other by direct physical means (electrically wired connection, mechanical interaction) or other indirect means (such as wireless RF, visible light, infrared, sound, ultrasound).

In lieu of a control system to control the therapy, the user can monitor the change in LV pressure while applying the neuromodulation therapy and fine tune the stimulation parameters described above to bring the LV relaxation rate to a desired level.

The system may be used to neuromodulate or stimulate cardiac parasympathetic nerve fibers for enhancing LV relaxation and to optionally decrease or sustain the heart rate. Electrode placement sites described in the prior patents and applications incorporated herein (e.g. U.S. Pat. No. 9,067,071 and U.S. patent application Ser. Nos. 14/642,699 and 14/801,560) may be used for the electrodes used to target those nerve fibers from within the vasculature.

The first embodiment may be used as a patient therapy in combination with administration with inotropes. As one example, the parasympathetic neuromodulation is administered to reduce heart rate and improve relaxation in combination with inotropes that increase heart rate and inadequately increase relaxation. Here the neuromodulation counteracts the negative effects of inotropes, namely increased heart rate and the inadequate increase in relaxation.

Second Embodiment: System for Enhancing LV Contractility and LV Relaxation

In a second embodiment, neuromodulation is used to deliver a therapy that enhances both LVC and LVR to a similar degree. The neuromodulation may be carried out using one or more therapy elements positioned in intravascular sites, such as in venous blood vessels superior to the heart, with the therapy elements used to neuromodulate extravascular nerve fibers to achieve LVR and LVC enhancement. Suitable sites for the therapy elements include those described in described in U.S. patent application Ser. Nos. 14/642,699 and 14/801,560 or U.S. Pat. No. 9,067,071, such as the superior vena cava, left brachiocephalic vein, lower internal jugular vein, right brachiocephalic vein, azygos vein or azygos arch. Placement of therapy elements such as electrodes against the posterior portions of these blood vessels can be particularly advantageous for allowing capture of nerve fibers for LVR and LVC enhancement.

An example of a system in accordance with the second embodiment is a system having one or more sympathetic therapy elements in combination with the parasympathetic therapy element and the stimulator described as the first embodiment. In the second embodiment the sympathetic therapy element is adapted to be positioned where it can, when energized, capture a cardiac sympathetic nerve fiber. The stimulator is operable to energize the sympathetic therapy element to deliver energy to the sympathetic cardiac nerve fiber to increase LVC, leading to increased cardiac output (CO). As discussed in the '699 and '560 applications referenced above, neuromodulation systems of the type described in the Background section may be used to carry out a treatment to increase LV contractility for increased CO. Neuromodulation therapy using therapy elements positioned to capture cardiac branches of the vagus nerve and cardiac sympathetic nerve fibers may be employed to deliver a therapy having the simultaneous effect of both increasing LV contractility in systole and increasing LV relaxation in diastole.

Figure 2:
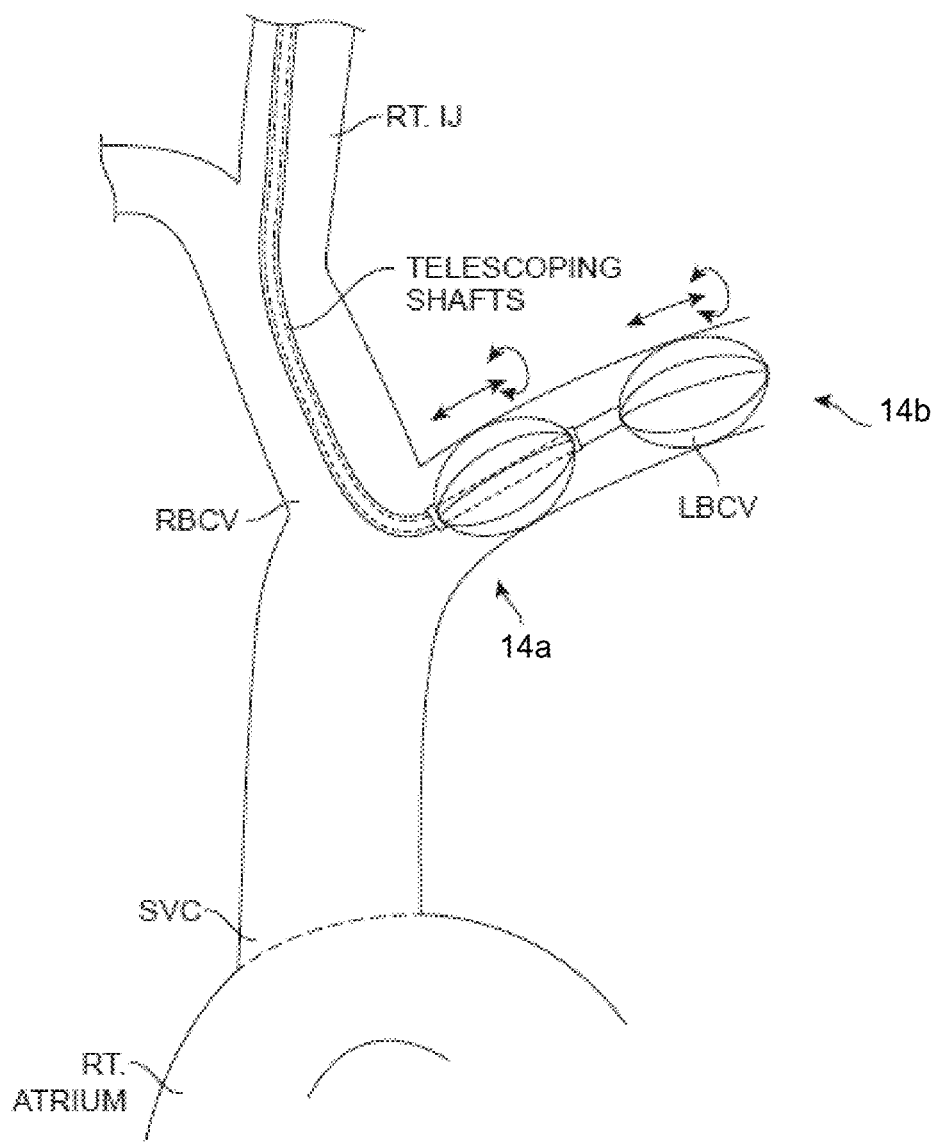
FIG. 2 shows a second embodiment of a neuromodulation system.

The sympathetic therapy elements may be on a common support with the parasympathetic therapy elements. For example, referring to FIG. 1, both the sympathetic and parasympathetic therapy elements may be on the support 14. Other configurations will have the sympathetic and parasympathetic therapy elements on different supports as shown in FIG. 2, which may optionally be on telescoping catheter shafts.

Measures that may be used for LVC and LVR include those described elsewhere in this application. For example, one measure of LVC that may be used in evaluating the change in LVC is the value dP/dt max of LVP rise in early systole taken prior to neuromodulation and after initiation of neuromodulation. One measure of LVR that may be used in evaluating the change in LVR is the rate dP/dt min of LVP drop in early diastole taken prior to neuromodulation and after initiation of neuromodulation.

The system may use a control system used to control the therapy to enhance both LVC and LVR. In general, it is desirable for LVR and LVC to be enhanced to a similar degree so that one is not be largely out of proportion to the other. The user may thus give input to the system selecting the ratio of LVC enhancement to LVR enhancement (each value of enhancement determined as described above). In a study conducted by the inventors of the present invention, the parasympathetic and sympathetic neuromodulation therapy performed using intravascular electrodes simultaneously increased a patient's LVC by +17% and LVR by +25%, for a ratio of LVC enhancement to LVR enhancement of 17/25=0.68. In contrast, administration of the inotrope Dobutamine, in the same patient in the absence of neuromodulation, increased LVC by 151% and LVR 54%, for a ratio of 2.8.

In general, ratios of LVC enhancement to LVR enhancement of 0.5-1.5 are desirable, with ratios of 0.8-1.2 more preferred and ratios of approximately 1 being most preferred. The magnitude of the desired ratio of LVC enhancement to LVR enhancement may depend on the clinical context. For example:

High LVC/LVR augmentation ratios (>=1.5) are useful in hemodynamic scenarios where cardiac output is low and more forward flow out of the left ventricle is preferred over pulmonary congestion relief. These may include Heart Failure with reduced ejection fraction (HFrEF) where CO is low, end organ perfusion is compromised, and there is a want for increased blood pressure. These ratios may also be useful when weaning from mechanical circulatory support (e.g. a blood pump) (MCS) or inotrope support.

LVC/LVR augmentation ratios close to 1 (0.8-1.2) are useful in hemodynamic scenarios where cardiac output is low, pulmonary congestion is high and both forward flow and congestion relief are preferred. Many HF patients would benefit from this.

Low LVC/LVR augmentation ratios (<0.5) are useful in hemodynamic scenarios where cardiac output is preserved and perfusion is adequate but pulmonary congestion relief is desired. These may include Heart failure with preserved ejection fraction (HFpEF) or in combination with other forward flow augmentation therapies such as an inotrope or MCS (discussed below in the section "Combination Therapies").

The control system of the second embodiment is similar to that of the first, and so the discussion of the control system above is incorporated by reference into the present discussion. The control system of the second embodiment additionally includes a Sympathetic Control function which generates the sympathetic therapeutic stimuli, and a Sympathetic Stimulation Output function that works with the Parasympathetic Control function to implement the system's overall function based on the user inputs (target LVC/LVR enhancement ratio) and feedback from patient sensed or hemodynamic parameters. The Parasympathetic and Sympathetic Control functions directly govern the therapeutic output from Parasympathetic and Sympathetic Output functions, respectively, by controlling the therapeutic levels, timing, polarity etc. The Control functions are responsible for the closed-loop modulation of the LVC/LVR enhancement ratio utilizing the user-targeted LVC/LVR enhancement ratio, as well as the feedback from actual LVC (measured for example by the rate dP/dt max of left ventricle pressure rise in early systole) and LVR (as measured for example by the rate dP/dt min of LV pressure drop in early diastole).

In lieu of a control system to control the therapy, the user can monitor the change in LV pressure during systole and diastole while applying the neuromodulation therapy and fine tune the stimulation parameters described above to bring the LVC/LVR enhancement ratio into the desired range.

The system may be used to deliver therapy of the type described in incorporated U.S. Pat. No. 9,067,071 to target sympathetic and parasympathetic nerve fibers to achieve both increased LVC and increased LVR. In particular, the therapy is directed to stimulate or neuromodulate cardiac sympathetic nerves for enhancing LV contractility, and to neuromodulate or stimulate cardiac parasympathetic nerves for enhancing LV relaxation. Electrode placement sites described in the prior patents and applications incorporated herein (e.g. U.S. Pat. No. 9,067,071 and U.S. patent application Ser. Nos. 14/642,699 and 14/801,560) may be used for the electrodes used to target those nerve fibers from within the vasculature. Thus, electrodes may be positioned in a common blood vessel (e.g. left brachiocephalic vein), and neuromodulation therapy delivered to enhance both LV relaxation and LV contractility to similar order of magnitude thus achieving a sympathovagal balance that favors similar increases in contractility and relaxation.

Alternatively, electrodes used to capture cardiac sympathetic nerves and electrodes used to capture cardiac parasympathetic nerves may deliver therapy from within separate blood vessels. The electrodes used for the sympathetic and parasympathetic nerve capture may be energized simultaneously or at different times (e.g. alternated).

Combination Therapies

Examples of therapeutic interventions using the disclosed systems in combination with other therapies will next be described.

Combination of LVR Enhancement and Mechanical Circulatory Support

Figure 3:
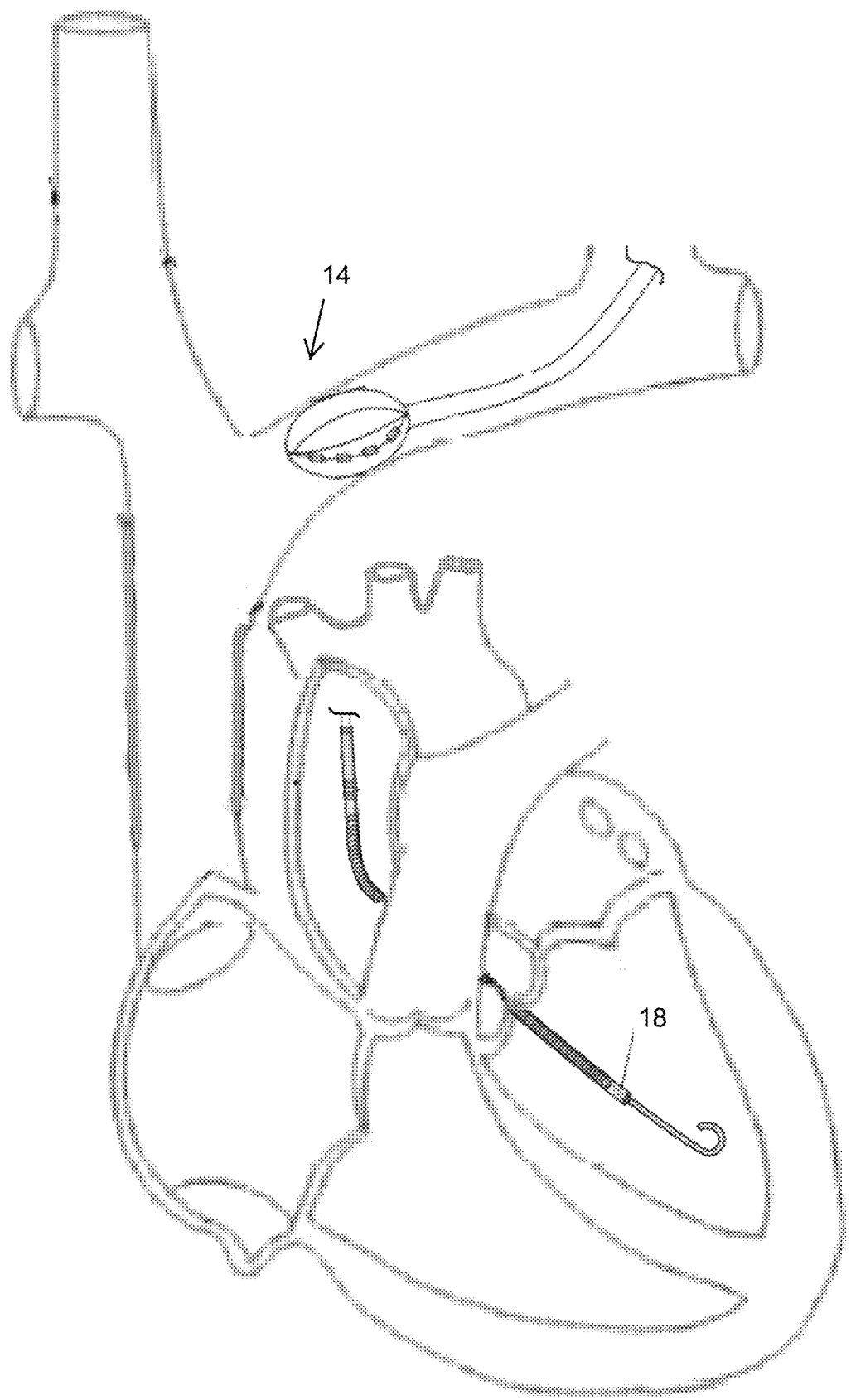
FIG. 3 shows the neuromodulation system of FIG. 1 in use as a combined therapy with a percutaneous blood pump in the left ventricle.

In a first type of combination therapy, neuromodulation of parasympathetic nerve fibers may be used to enhance relaxation in patients who are not undergoing neuromodulation of cardiac sympathetic nerve fibers. For example, neuromodulation using intravascular therapy elements to enhance relaxation using the system of FIG. 1 may be used in combination with other therapies directed towards increasing CO. Exemplary therapies that may be combined with the disclosed method for enhancing relaxation including use of hemodynamic support devices that increase the volume of blood moving through the heart in order to increase cardiac output CO. Such devices include percutaneous ventricular assist devices (PVAD), ventricular assist devices (VAD) or intra-aortic balloon pumps (IABP) for increasing CO. See for example FIG. 3, which shows neuromodulation therapy element 14 in the left brachiocephalic vein for use in capturing a parasympathetic nerve fiber to enhance LV relaxation, together with a PVAD 18. Where mechanical circulatory support devices are described herein, sensors used to determine the measures of LVR and LVC may optionally be positioned on the support devices themselves. For example, a sensor on a PVAD device disposed within the heart as shown in FIG. 3 may include a sensor positioned within the left ventricle. This sensor can be used to determine left ventricular pressure to aid in the determination of dP/dt min in diastole and dP/dt max in systole as described above.

Combination of LVR and HR Decrease and Mechanical Circulatory Support

In a modification of the prior example, neuromodulation of parasympathetic nerve fibers is used to both decrease heart rate and improve relaxation in patients who are not undergoing neuromodulation of cardiac sympathetic nerve fibers. For example, neuromodulation to reduce heart rate and improve relaxation may be used in combination with other therapies directed towards unloading and resting the heart to more fully unload or rest the heart. Such devices include percutaneous ventricular assist devices (PVAD), ventricular assist devices (VAD) or intra-aortic balloon pumps (IABP) for more fully unloading and resting the heart. See for example FIG. 3, which shows neuromodulation therapy element 14 in the left brachiocephalic vein for use in capturing a parasympathetic nerve fiber to enhance LV relaxation and lowering the heart rate, together with a PVAD 18.

A blood pump (i.e. PVAD or IABP) mechanically rests the heart, but it does not alter heart rate which is the other main determinant of oxygen consumption. By combining a therapy that mechanically unloads the heart with therapy that reduces heart rate and improved relaxation ("neuromechanically unloading") the heart can be rested and unloaded more fully than can be achieved using a catheter-mounted pump alone. Small percutaneously placed pumps such as PVAD or IABP pumps achieve a relatively small amount of unloading or resting compared with larger surgically placed pumps. Combining the use of catheter-mounted pumps with the disclosed neuromodulation can result in neuromechanical unloading sufficient to allow a small catheter pump to be used when a large surgical pump would otherwise have been needed to more fully rest and unload the heart.

Other Combinations

In general, neuromodulation systems of the type referred to in the patents and applications incorporated here may be used in combination with other therapies intended for cardiac effect. In addition to those described in the preceding paragraph, other examples include:

parasympathetic neuromodulation to enhance parasympathetic tone, in combination with catheter-mounted pumps for increasing CO sympathetic with or without parasympathetic neuromodulation to enhance cardiac output, in combination with beta blockers in order to further lower heart rate and further improve myocardial energetics.

parasympathetic neuromodulation to reduce arrhythmias in combination with inotropes that increase arrhythmias (improving or counteracting the negative effects of inotropes, which are increased arrhythmias, increased heart rate and the inadequate increase in relaxation).

All patents and patent applications referred to herein, including for purposes of priority, are incorporated herein by references for all purposes.

We claim:

1. A method of treating a patient having a left ventricular contractility (LVC) and a left ventricular relaxation (LVR), comprising:
   administering an inotropic agent to the patient to enhance LVC and delivering neuromodulation therapy to the patient to contemporaneously enhance LVR, such that the ratio of the enhancement of LVC to the enhancement of LVR is within a predetermined range, wherein the enhancement of LVR is determined by determining the increase in a value selected from dP/dt min in diastole, arterial blood pressure (ABP) in diastole, tau in diastole, mitral valve deceleration time or mitral valve velocity time interval from prior to initiation of neuromodulation to after initiation of neuromodulation.

2. The method of claim 1, wherein the neuromodulation therapy includes:
   using a therapy element positioned in an intravascular location to neuromodulate at least one extravascular nerve fiber to increase LVR.

3. The method of claim 2, wherein the intravascular location is selected from the group of blood vessels consisting of the superior vena cava, left brachiocephalic vein and right brachiocephalic vein.

4. The method of claim 2, wherein the intravascular location is selected from the group of blood vessels consisting of the superior vena cava, left brachiocephalic vein, lower internal jugular vein, right brachiocephalic vein, azygos vein or azygos arch.

5. The method of claim 1, wherein the neuromodulation therapy is delivered to enhance LVR such that the ratio of the percentage increase of LVC to the percentage increase of LVR is within a predetermined range.

6. The method of claim 5, wherein the predetermined range is 0.5-1.5.

7. The method of claim 5, wherein the predetermined range is 0.8-1.2.

8. The method of claim 5, wherein the predetermined range is approximately 1.0.

9. The method of claim 1 wherein the method includes automatically adjusting at least one neuromodulation parameter such that the ratio of the enhancement of LVC to the enhancement of LVR is within the predetermined range.

10. The method of claim 9, wherein the therapy elements are electrodes and the neuromodulation parameter adjusted by the system is at least one of electrical currents, voltages, and pulse widths, pulse frequency, charge density, effective electrode surface area, effective electrode spacing, and electrode combinations energized.

11. A method of treating a patient having a left ventricular contractility (LVC) and a left ventricular relaxation (LVR), comprising:

administering an inotropic agent to the patient to enhance LVC and delivering neuromodulation therapy to the patient to contemporaneously enhance LVR, such that the ratio of the enhancement of LVC to the enhancement of LVR is within a predetermined range, wherein the enhancement of LVC is determined by determining the increase in the value selected from dP/dt max in systole, ABP in systole, from prior to initiation of neuromodulation to after initiation of neuromodulation.

12. The method of claim 11, wherein the neuromodulation therapy includes:

using a therapy element positioned in an intravascular location to neuromodulate at least one extravascular nerve fiber to increase LVR.

13. The method of claim 12, wherein the intravascular location is selected from the group of blood vessels consisting of the superior vena cava, left brachiocephalic vein and right brachiocephalic vein.

14. The method of claim 12, wherein the intravascular location is selected from the group of blood vessels consisting of the superior vena cava, left brachiocephalic vein, lower internal jugular vein, right brachiocephalic vein, azygos vein or azygos arch.

15. The method of claim 11, wherein the neuromodulation therapy is delivered to enhance LVR such that the ratio of the percentage increase of LVC to the percentage increase of LVR is within a predetermined range.

16. The method of claim 15, wherein the predetermined range is 0.5-1.5.

17. The method of claim 15, wherein the predetermined range is 0.8-1.2.

18. The method of claim 15, wherein the predetermined range is approximately 1.0.

19. The method of claim 11 wherein the method includes automatically adjusting at least one neuromodulation parameter such that the ratio of the enhancement of LVC to the enhancement of LVR is within the predetermined range.

20. The method of claim 11, wherein the therapy elements are electrodes and the neuromodulation parameter adjusted by the system is at least one of electrical currents, voltages, and pulse widths, pulse frequency, charge density, effective electrode surface area, effective electrode spacing, and electrode combinations energized.

* * * * *